(12) United States Patent
Melsheimer

(10) Patent No.: US 7,731,693 B2
(45) Date of Patent: Jun. 8, 2010

(54) COUPLING WIRE GUIDE

(75) Inventor: Jeffry S. Melsheimer, Springville, IN (US)

(73) Assignee: Cook Incorporated, Bloomington, IN (US)

( * ) Notice: Subject to any disclaimer, the term of this patent is extended or adjusted under 35 U.S.C. 154(b) by 529 days.

(21) Appl. No.: 11/549,473

(22) Filed: Oct. 13, 2006

(65) Prior Publication Data

US 2007/0100257 A1  May 3, 2007

Related U.S. Application Data

(60) Provisional application No. 60/730,582, filed on Oct. 27, 2005.

(51) Int. Cl.
*A61M 5/178* (2006.01)
*A61M 25/00* (2006.01)
*A61B 17/24* (2006.01)
*A61B 17/26* (2006.01)

(52) U.S. Cl. .................. 604/164.13; 600/585; 606/113

(58) Field of Classification Search ................. 600/585; 606/113; 604/164.13
See application file for complete search history.

(56) References Cited

U.S. PATENT DOCUMENTS

| 2,657,691 | A | | 11/1953 | Nordstrom, Jr. |
| 3,521,620 | A | | 7/1970 | Cook |
| 3,547,103 | A | | 12/1970 | Cook |
| 3,656,680 | A | | 4/1972 | Nomura |
| 3,739,784 | A | * | 6/1973 | Itoh ............................ 606/113 |
| 3,890,997 | A | | 6/1975 | Wilson |
| 4,548,206 | A | | 10/1985 | Osborne |
| 4,569,347 | A | | 2/1986 | Frisbie |
| 4,601,713 | A | | 7/1986 | Fuqua |
| 4,650,472 | A | | 3/1987 | Bates |
| 4,665,906 | A | | 5/1987 | Jervis |
| 4,824,435 | A | | 4/1989 | Giesy et al. |
| 4,921,483 | A | | 5/1990 | Wijay et al. |
| 4,925,445 | A | | 5/1990 | Sakamoto et al. |

(Continued)

FOREIGN PATENT DOCUMENTS

EP   0 436 303 A1   11/1990

(Continued)

OTHER PUBLICATIONS

The Journal of Invasive Cardiology entitled "Use of a Second Buddy Wire During Percutaneous Coronary Interventions: A Simple Solution for Some Challenging Situations" dated Apr. 25, 2005, pp. 1-8.

(Continued)

*Primary Examiner*—Nicholas D Lucchesi
*Assistant Examiner*—Rebecca E Eisenberg
(74) *Attorney, Agent, or Firm*—Brinks Hofer Gilson & Lione

(57) ABSTRACT

A coupling wire guide structured to be slidably coupled to a previously introduced wire guide. The coupling wire guide includes a main body having a distal section. The distal section includes an outer wire disposed over a safety wire. A loop wire is connected to the safety wire at two axially spaced points. At least a portion of the loop wire is positioned outside of the outer wire to define a loop area sized to receive the previously introduced wire guide.

16 Claims, 2 Drawing Sheets

U.S. PATENT DOCUMENTS

| | | | |
|---|---|---|---|
| 4,934,380 A | 6/1990 | De Toledo |
| 4,984,581 A | 1/1991 | Stice |
| 5,003,990 A | 4/1991 | Osypka |
| 5,069,226 A | 12/1991 | Yamauchi et al. |
| 5,105,818 A | 4/1992 | Christian et al. |
| 5,129,890 A | 7/1992 | Bates et al. |
| 5,131,407 A | 7/1992 | Ischinger et al. |
| 5,159,861 A | 11/1992 | Anderson |
| 5,213,111 A | 5/1993 | Cook et al. |
| 5,234,003 A | 8/1993 | Hall |
| 5,242,759 A | 9/1993 | Hall |
| 5,243,996 A | 9/1993 | Hall |
| 5,251,640 A | 10/1993 | Osborne |
| 5,267,958 A | 12/1993 | Buchbinder et al. |
| 5,306,261 A | 4/1994 | Alliger et al. |
| 5,318,527 A | 6/1994 | Hyde et al. |
| 5,325,746 A | 7/1994 | Anderson |
| 5,328,472 A | 7/1994 | Steinke et al. |
| 5,328,480 A | 7/1994 | Melker et al. |
| 5,344,413 A | 9/1994 | Allman et al. |
| 5,354,257 A | 10/1994 | Roubin et al. |
| 5,383,853 A | 1/1995 | Jung et al. |
| 5,402,799 A | 4/1995 | Colon et al. |
| 5,449,362 A | 9/1995 | Chaisson et al. |
| 5,456,680 A | 10/1995 | Taylor et al. |
| 5,488,959 A | 2/1996 | Ales |
| 5,597,378 A | 1/1997 | Jervis |
| 5,667,521 A | 9/1997 | Keown |
| 5,738,667 A | 4/1998 | Solar |
| 5,762,070 A | 6/1998 | Nagamatsu |
| 5,776,079 A | 7/1998 | Cope et al. |
| 5,776,100 A | 7/1998 | Forman |
| 5,797,857 A | 8/1998 | Obitsu |
| 5,810,876 A | 9/1998 | Kelleher |
| 5,827,225 A | 10/1998 | Ma Schwab |
| 5,873,842 A | 2/1999 | Brennen et al. |
| 5,882,333 A | 3/1999 | Schaer et al. |
| 5,891,056 A | 4/1999 | Ramzipour |
| 5,893,868 A | 4/1999 | Hanson et al. |
| 5,993,424 A | 11/1999 | Lorenzo et al. |
| 5,997,526 A | 12/1999 | Giba et al. |
| 6,007,517 A | 12/1999 | Anderson |
| 6,139,510 A | 10/2000 | Palermo |
| 6,217,567 B1 | 4/2001 | Zadno-Azizi et al. |
| 6,221,066 B1 | 4/2001 | Ferrera et al. |
| 6,248,092 B1 | 6/2001 | Miraki et al. |
| 6,254,549 B1 | 7/2001 | Ramzipoor |
| 6,254,550 B1 | 7/2001 | McNamara et al. |
| 6,290,693 B1 | 9/2001 | Jung, Jr. et al. |
| 6,306,141 B1 | 10/2001 | Jervis |
| 6,309,404 B1 | 10/2001 | Krzyzanowski |
| 6,348,041 B1 | 2/2002 | Klint |
| 6,348,045 B1 | 2/2002 | Malonek et al. |
| 6,383,146 B1 | 5/2002 | Klint |
| 6,471,697 B1 | 10/2002 | Lesh |
| 6,475,167 B1 | 11/2002 | Fleming et al. |
| 6,500,130 B2 | 12/2002 | Kinsella et al. |
| 6,502,606 B2 | 1/2003 | Klint |
| 6,517,518 B2 | 2/2003 | Nash et al. |
| 6,530,899 B1 | 3/2003 | Savage |
| 6,569,151 B1 | 5/2003 | Nash et al. |
| 6,596,963 B2 | 7/2003 | Kelly |
| 6,605,049 B1 | 8/2003 | Wagner et al. |
| 6,613,002 B1 | 9/2003 | Clark et al. |
| 6,638,372 B1 | 10/2003 | Abrams et al. |
| 6,682,608 B2 | 1/2004 | Abrams et al. |
| 6,805,676 B2 | 10/2004 | Klint |
| 6,872,192 B2 | 3/2005 | Nash et al. |
| 7,074,197 B2 | 7/2006 | Reynolds et al. |
| 7,076,285 B2 | 7/2006 | Windheuser et al. |
| 7,229,431 B2 | 6/2007 | Houser et al. |
| 2002/0058888 A1 | 5/2002 | Biagtan et al. |
| 2002/0169457 A1 | 11/2002 | Quinn |
| 2003/0028127 A1 | 2/2003 | Balzum et al. |
| 2003/0120208 A1 | 6/2003 | Houser et al. |
| 2004/0073108 A1 | 4/2004 | Saeed et al. |
| 2004/0116957 A1 | 6/2004 | Nishide |
| 2004/0199087 A1* | 10/2004 | Swain et al. ................ 600/585 |
| 2004/0215208 A1 | 10/2004 | Foushee et al. |
| 2005/0027212 A1 | 2/2005 | Segner et al. |
| 2005/0075647 A1 | 4/2005 | Walters et al. |
| 2005/0143770 A1 | 6/2005 | Carter et al. |
| 2005/0148902 A1 | 7/2005 | Minar et al. |
| 2005/0197663 A1 | 9/2005 | Soma et al. |
| 2005/0209533 A1 | 9/2005 | Lorenz |
| 2006/0100544 A1 | 5/2006 | Ayala et al. |
| 2006/0100545 A1 | 5/2006 | Ayala et al. |
| 2007/0060908 A1 | 3/2007 | Webster et al. |
| 2007/0167065 A1 | 7/2007 | Melsheimer et al. |
| 2007/0185414 A1 | 8/2007 | Urbanski et al. |
| 2007/0191790 A1 | 8/2007 | Eells et al. |

FOREIGN PATENT DOCUMENTS

| | | |
|---|---|---|
| EP | 0829269 A1 | 3/1998 |
| EP | 1057500 A1 | 12/2000 |
| EP | 1 428 546 A2 | 6/2004 |
| WO | WO 93/14805 | 8/1993 |
| WO | WO 96/10436 | 4/1996 |
| WO | WO 99/44510 | 9/1999 |
| WO | WO 00/74565 A1 | 12/2000 |
| WO | WO 01/03764 A1 | 1/2001 |
| WO | WO 02/094364 A2 | 11/2002 |
| WO | WO2004/033016 | 4/2004 |
| WO | WO 2004/049970 A2 | 6/2004 |
| WO | WO 2004/050161 A1 | 6/2004 |
| WO | WO 2005/011530 A1 | 2/2005 |
| WO | WO 2005/011788 A1 | 2/2005 |
| WO | WO 2005/025660 A1 | 3/2005 |
| WO | WO 2005/089852 A1 | 9/2005 |
| WO | WO 2006/039216 A2 | 4/2006 |
| WO | WO 2007/084474 A1 | 7/2007 |
| WO | WO 2007/089891 A1 | 8/2007 |
| WO | WO 2007/089893 A1 | 8/2007 |

OTHER PUBLICATIONS

International Search Report & Written Opinion (Jan. 3, 2008).
Notification of Transmittal of International Preliminary Report on Patentability (Jan. 10, 2008).
Office Action dated Mar. 17, 2008 U.S. Appl. No. 11/706,548 issued in related application.
Office Action dated Apr. 7, 2008 U.S. Appl. No. 11/699,174 issued in related application.
Office Action dated May 16, 2008 U.S. Appl. No. 11/763,355 issued in related application.
Office Action dated May 30, 2008 U.S. Appl. No. 11/507,805 issued in related application.
Office Action dated May 23, 2008 U.S. Appl. No. 11/652,430 issued in related application.
International Search Report—PCT/US2007/04827 & Opinion (Mar. 14, 2008).
Suppl) Notification of Transmittal of International Preliminary Report on Patentability—PCT/US2007/002743—(Jun. 3, 2008).
Office Action Restriction dated Mar. 3, 2008 U.S. Appl. No. 11/507,805 issued in related application.
Office Action Restriction dated Jul. 2, 2008 U.S. Appl. No. 11/699,171 issued in related application.
International Search Report/Written Opinion—PCT/US2006/040843 (Feb. 7, 2007).
International Preliminary Report on Patentability—PCT/US2007/002741 (Jun. 25, 2008).
International Search Report—PCT/US2006/040843 (Jan. 31, 2007).
International Search Report—PCT/US2007/002743 (Jun. 14, 2007).
International Search Report—PCT/US2007/002741 (Jul. 9, 2007).

Office Action dated Nov. 15, 2007 issued in related U.S. Appl No. 11/652,430.
Office Action dated Oct. 20, 2008 U.S. Appl. No. 11/549,481 issued in co-pending application.
Office Action dated Oct. 28, 2008 U.S. Appl. No. 11/507,805 issued in co-pending application.
Office Action dated Nov. 20, 2008 U.S. Appl. No. 11/763,355 issued in co-pending application.
Office Action dated Nov. 21, 2008 U.S. Appl. No. 11/699,171 issued in co-pending application.
Office Action dated Dec. 11, 2008 U.S. Appl. No. 11/652,430 issued in co-pending application.
Advisory Action dated Jan. 16, 2009 U.S. Appl. No. 11/507,805 issued in co-pending application.
Advisory Action dated Mar. 6, 2009 U.S. Appl. No. 11/652,430 issued in co-pending application.
Office Action dated Mar. 30, 2009 U.S. Appl. No. 11/699,174 issued in co-pending application.
Office Action dated Apr. 1, 2009 U.S. Appl. No. 11/507,805 issued in co-pending application.
Office Action dated Apr. 7, 2009 U.S. Appl. No. 11/706,548 issued in co-pending application.
Office Action dated Apr. 14, 2009 U.S. Appl. No. 11/549,481 issued in co-pending application.
Office Action dated May 8, 2009 U.S. Appl. No. 11/699,171 issued in co-pending application.
Office Action dated May 14, 2009 U.S. Appl. No. 11/507,993 issued in coo-pending application.
International Search Report—PCT/US2006/042184 (Mar. 1, 2007).
International Search Report—PCT/US2007/001066 (Jun. 18, 2007).
International Search Report—PCT/US2007/004827 (Oct. 26, 2007).

* cited by examiner

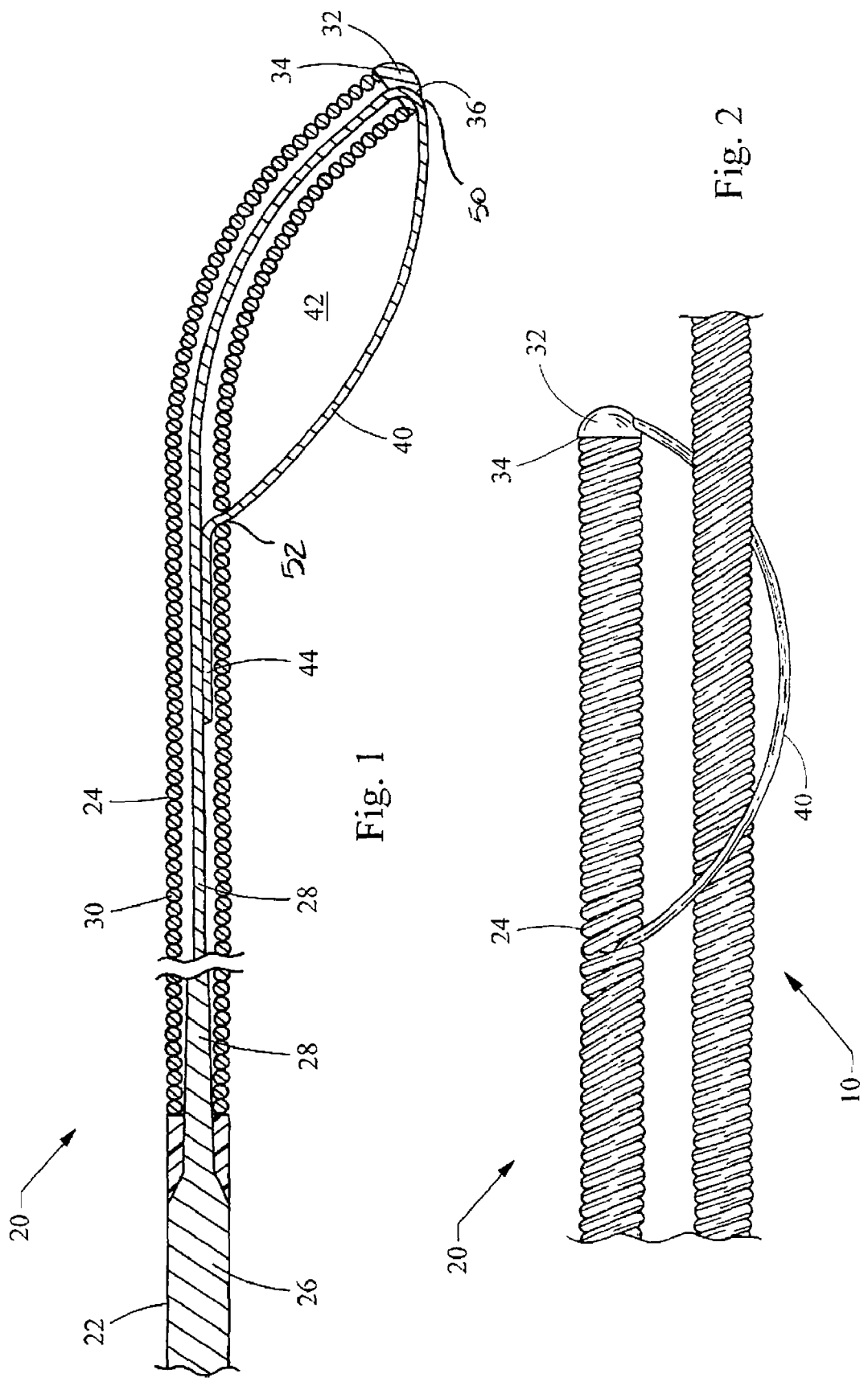

COUPLING WIRE GUIDE

CROSS-REFERENCE TO RELATED APPLICATIONS

This application claims the benefit of U.S. Provisional Application Ser. No. 60/730,582 filed on Oct. 27, 2005, entitled "COUPLING WIRE GUIDE", the entire contents of which are incorporated herein by reference.

FIELD OF THE INVENTION

This invention relates generally to a wire guide for use in intracorporeal procedures, and more particularly relates to the construction of a wire guide to be coupled to a previously introduced wire guide for assistance during interventional procedures in vessels with proximal tortuosity, or as a more substantial wire guide for angioplasty procedures, stenting procedures, and other device placement procedures and their related devices.

BACKGROUND OF THE INVENTION

Proximal tortuosity of the vasculature is problematic for all medical catheter devices such as atherectomy devices, angioplasty devices, stent delivery devices, and filter delivery devices. Wire guides are therefore typically used to navigate the vasculature of a patient during percutaneous interventional procedures. Once the wire guide has been introduced, it may then be used to introduce one or more medical catheter devices. Thus, most wire guides are typically 0.014 inches in diameter and have a lubricious coating to enhance wire guide introduction movement. Conventional 0.014 inch floppy wire guides must have sufficient flexibility and torque control for navigation through tortuous vessels. At the same time, the wire guide must have a certain amount of rigidity to pass through lesions, straighten extremely tortuous vessels, and support medical catheter devices that are introduced over the wire guide.

Accordingly, wire guides are subjected to potentially conflicting requirements. Conventional 0.014 inch floppy wire guides are usually sufficient for navigation of moderately tortuous vessels. However, in some situations the wire guide tip may prolapse away from the site to which it is guiding the device. For example, balloon angioplasty in vessels with proximal tortuosity has been associated with a higher incidence of acute complications and procedural failure due to the inability to cross lesions with a conventional floppy wire guide, and due to the inability of the wire guide to provide adequate support to the balloon catheter. Heavy-duty wire guides, on the other hand, are generally not well suited as primary wire guides because of their stiffness and potential for causing injury to the vessel during introduction.

It may therefore be desirable to use conventional floppy wire guides for navigation of tortuous vessels, and then enhance the conventional wire guide with a supplemental wire guide. The supplemental wire guide will straighten out the vessel curves and ease further wire guide movement. Additionally, the supplemental wire guide provides greater support and enhances the tracking of balloons, stents, stent delivery devices, atherectomy devices, and other medical catheter devices as compared to a conventional floppy wire guide. This technique is commonly referred to as the "Buddy Wire" technique, details of which are disclosed in U.S. patent application Ser. No. 11/081,146, filed Mar. 16, 2005.

However, the navigation of the supplemental wire guide parallel to the first wire guide is an exacting and time consuming process in which additional difficulties are encountered. For example, the second wire guide can cork screw or coil around the first wire guide, which may result in immobilization or unintended movement of the first wire guide, which in turn may require the retraction and re-feeding of the supplemental wire guide and/or the primary wire guide. Moreover, if retraction of the supplemental wire guide is necessary, either of the wire guides may become contaminated and the entire process may need to be restarted with sterile components. The time consumed by this process can be critical to the success of the procedure. Additionally, when traversing through the heart of a patient, and particularly the ostium, the larger open space of the heart makes identical placement of the supplemental wire guide somewhat difficult.

Accordingly, there exists a need to provide a supporting wire guide for percutaneous interventional procedures that may be easily and reliably traversed through the vasculature to a position proximate a previously introduced wire guide.

BRIEF SUMMARY OF THE INVENTION

The present invention provides a supporting wire guide for intracorporeal procedures that may be easily and reliably traversed through the vasculature to a position proximate a previously introduced wire guide. The supporting wire guide is a coupling wire guide that is structured to be slidably coupled to the previously introduced wire guide. In one embodiment constructed in accordance with the teachings of the present invention, the coupling wire guide generally includes a main body having a distal section. The distal section includes an outer wire disposed over a safety wire. A loop wire is connected to the safety wire at two axially spaced points. At least a portion of the loop wire is positioned outside of the outer wire to define a loop area sized to receive the previously introduced wire guide.

According to more detailed aspects, the length of the loop wire is preferably greater than or equal to the distance along the safety wire between the two axially spaced points, and most preferably greater than or equal to the distance along the safety wire between the two axially spaced points plus the circumference of the previously introduced wire guide. The safety wire is typically connected to an end cap defining a distal tip of the coupling wire guide, and the end cap may include a passageway through which the loop wire extends. The proximal end of the loop wire projects through adjacent winds of the coiled outer wire. When the loop wire does not extend through the end cap, the loop wire projects through adjacent winds of the coiled wire at two locations proximate the two axially spaced points. The main body may take many forms, including a mandrel or a coiled wire.

The loop wire may comprise a separate and individually formed wire having ends connected to the safety wire, or alternatively a distal portion of the safety wire may itself form the loop wire. In the latter case, the distal portion of the safety wire projects out of the outer wire, extends proximally, and projects back within the outer wire. Preferably, the distal portion of the safety wire extends through a passageway formed in the end cap. The passageway in the end cap preferably opens on a radially facing side of the end cap. The portion of the safety wire positioned outside of the outer wire is sized to permit the main body and distal section to extend in a straight axial line while maintaining a looped area sized to receive the previously introduced wire guide.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 1 is a sectional side view of a coupling wire guide constructed in accordance with the teachings of the present invention;

FIG. 2 is a side view of the coupling wire guide depicted in FIG. 1 shown coupled to a previously introduced wire guide.

DETAILED DESCRIPTION OF THE INVENTION

Figure 3:
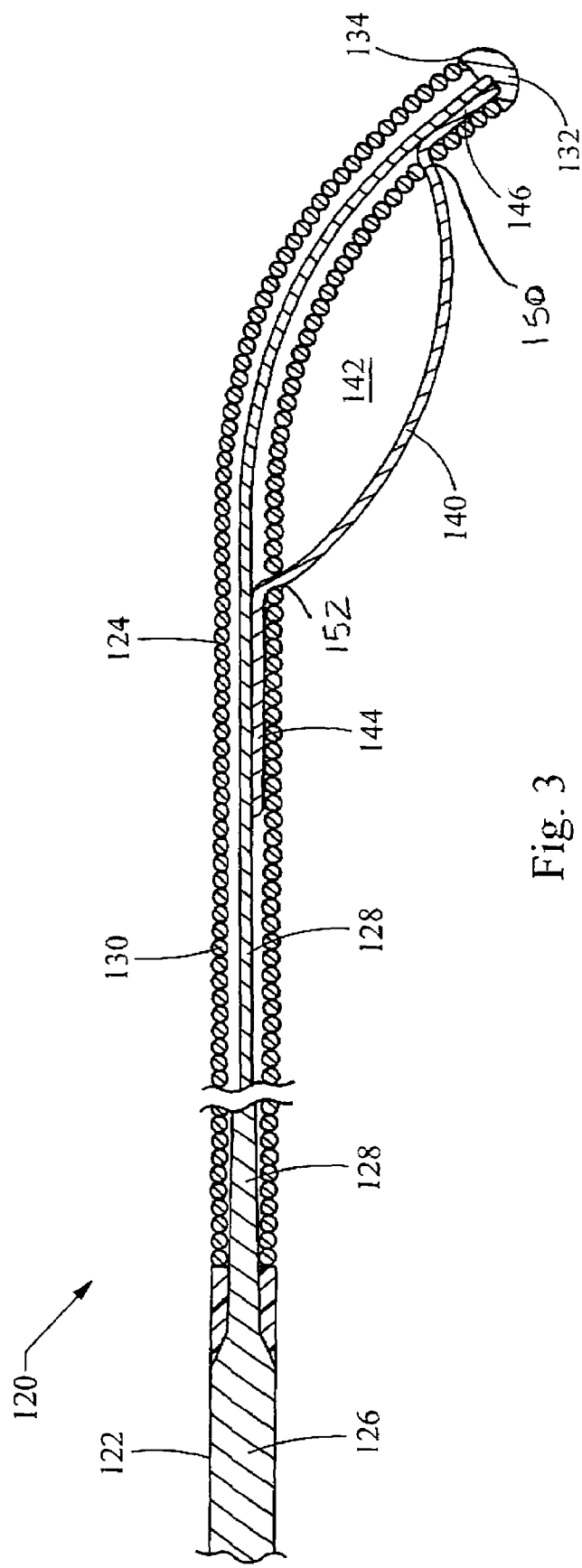
FIG. 3 is a sectional side view of an alternate embodiment of the coupling wire guide depicted in FIG. 1.

Turning now to the figures, FIGS. 1 and 2 depict a coupling wire guide 20 constructed in accordance with the teachings of the present invention. The coupling wire guide 20 includes a main body 22 having a distal section 24. The main body 22 has been shown as a mandrel 26, a structure well known in the art. In the area of the distal section 24, the mandrel 26 narrows to define a safety wire 28 over which an outer wire 30 is disposed. Specifically, the outer wire 30 is coiled over the safety wire 28, which in turn is connected to an end cap 32 to define a distal tip 34 of the coupling wire guide 20.

The coupling wire guide 20 is structured for coupling to a previously introduced wire guide, which is depicted in FIG. 2 as a coiled wire 10. It will be recognized that the previously introduced wire guide 10, as well as the main body 22 of the coupling wire guide 20, may take numerous forms as many types of wire guides are known in the art, including a solid wire, tubular wires, coiled wires and combinations thereof. For example, the main body 22 may comprise the coiled outer wire 30 disposed over an elongated safety wire 28. Likewise, the previously introduced wire guide 10 may simply comprise a mandrel alone or a combination of mandrel and coiled wire, similar to the coupling wire guide 20 and as is shown in U.S. Pat. No. 5,243,996, the disclosure of which is incorporated herein by reference in its entirety. While wire guides are often used in percutaneous interventional procedures, it will be recognized by those skilled in the art that the wire guides of the present invention may also be employed in endoscopic or other intracorporeal procedures.

The distal section 24 of the coupling wire guide 20 includes a loop wire 40 which is positioned outside of the outer wire 30 to define a loop area 42 sized to receive the previously introduced wire guide 10. In this embodiment, the loop wire 40 is formed by a distal portion of the safety wire 28. At the distal tip 34 of the coupling wire guide 20, the end cap 32 includes a passageway 36 through which the safety wire 28 extends. The passageway 36 of the end cap 32 opens radially on a side of the end cap 32, where the safety wire 28 projects at point 50 to form the distal portion of the loop wire 40. The loop wire 40 extends along the exterior of the outer wire 30 a predetermined distance. The proximal end of the loop wire 40 passes through the outer wire 30 between two adjacent winds of the wire 30 at a position 52 axially spaced (proximally) from the end cap 32 and its passageway 36. That is, the safety wire 28 projects out of and away from the distal tip 34, extends proximally while positioned outside of the outer wire 30, and then projects back inside the outer wire 30 for connection onto to itself, thereby defining a loop area 42 for coupling. The end 44 of the loop wire 40 is connected to the safety wire 28, typically through soldering or welding although any well known connection methods or materials may be used. The safety wire 28 may also be fixedly attached to the end cap 32, such as by soldering or welding.

The coupling wire guide 20 has been depicted in FIG. 2 as coupled to a previously introduced wire guide 10. Although the distal section 24 of the coupling wire guide 20 is depicted as curved in FIG. 1, it is depicted as straight in FIG. 2 to more closely depict the shape of the coupling wire guide 20 as it is traversed through the vasculature along the previously introduced wire guide 10. As such, it will be recognized that the loop wire 40 has length greater than or equal to the distance along the safety wire 28 between the two axially spaced connection points 50, 52 of the loop wire 40, and most preferably greater than or equal to the distance, measured along the safety wire 28, between the two axially spaced connection points 50, 52 plus the circumference of the previously introduced wire guide 10. This permits the coupling wire guide 20 to maintain a substantially straight orientation that is generally parallel to the previously introduced wire guide 10. Further, the axial distance between the two connection points 50, 52 of the loop wire 40 is preferably greater than the diameter of the previously introduced wire guide 10. In this manner, the previously introduced wire guide 10 may be abutted directly against the coupling wire guide 20. The wire guides 10, 20 are coupled by placing a proximal end of the previously introduced wire guide 10 through the loop area 42 formed by the loop wire 40. The coupling wire guide 20 is then traversed through the vasculature in a normal manner, preferably while holding the previously introduced wire guide 10 in place. To decouple the wire guides 10, 20, the wire guides 10, 20 are moved relative to one another such that a distal end of the previously introduced wire guide 10 passes proximally through and is removed from the loop area 42 of the loop wire 40.

Accordingly, it will be recognized by those skilled in the art that the distal section 24 of the coupling wire guide 20, by way of loop wire 40, provides a simple and reliable slidable connection to a previously introduced wire guide 10. The loop area 42 provides a large space through which wire guides 10, 20 can be easily and quickly connected together. Since the loop wire 40 is of a relatively small diameter, a low profile is maintained for the coupling wire guide 20. Further, since the loop wire 40 projects radially away from the distal tip 34 at a side of the end cap 32, the atraumatic nature of the distal tip 34 is maintained. Furthermore, the coupling wire guide 20 is provided with sufficient flexibility that is helpful when traversing through the vasculature, especially tortuous pathways, and along the previously introduced wire guide 10. At the same time, a secure connection is formed between the wire guides 10, 20, and the distal section 24 has sufficient rigidity to translate the coupling wire guide 20 over the previously introduced wire guide 10 and pass through obstructed passageways, such as those having plaque or other lesions.

An alternate embodiment of the coupling wire guide 120 has been depicted in FIG. 3 and constructed in accordance with the teachings of the present invention. As in the prior embodiment, the coupling wire guide 120 includes a main body 122 defined by a mandrel 126, and a distal section 124 defined by a coiled wire 130. The mandrel 126 narrows to define a safety wire 128 over which the outer wire 130 is coiled. The safety wire 128 extends distally and is connected to an end cap 132 defining a distal tip 134 of the coupling wire guide 120.

In this embodiment, however, the loop wire 140 is a separately formed component from the safety wire 128. The loop wire 140 is largely positioned outside of the outer wire 130 to define a large loop area 142 for coupling to a previously introduced wire guide 10 (shown in FIG. 2). A first end 144 of the loop wire 140 is connected to the safety wire 128 at a first axial position 152, while a second end 146 of the loop wire 140 is connected to the safety wire 128 at a second axial position 150 proximate the distal tip 134. Preferably, the second end 146 of the loop wire 140 is also connected to the end cap 132 in a manner similar to the interconnection of the safety wire 128 and the end cap 132, such as soldering or welding as discussed in the prior embodiment.

It can be seen in FIG. 3 that the loop wire 140 extends through adjacent winds of the coiled outer wire 130 at two different axial locations proximate the two connection points 150, 152. As such, the exterior atraumatic shape of the distal tip 134 is maintained. It will also be recognized that in the previous embodiment described with reference to FIG. 1, where the loop wire 40 is unitarily formed with and by the safety wire 28, the wire 28 could double back within the coiled outer wire 30 before projecting out of the wire 30, thereby obviating the need to form the passageway 36 in the end cap 32. It will also be recognized that numerous other variations may be made to the depicted embodiments, such as moving the location of the loop wire 40, 140 and loop area 42, 142 either distally or proximally. Likewise, the length of the loop wire 40, 140 may be significantly greater than the distance between the two connection points to the safety wire 28, 128, and the loop wire 40, 140 can be of any size, limited only by the size of outer wire 30, 130 and the coupling wire guide 20, 120.

Accordingly, it will be recognized by those skilled in the art that the coupling wire guide provides simple and reliable coupling to a previously introduced wire guide through the provision of a loop area defined by a loop wire. At the same time, the distal section of the coupling wire guide is minimally altered to maintain the desired amounts of flexibility, rigidity and strength. In this manner, the coupling wire guide is increasingly adept at traversing the vasculature, and in particular tortuous pathways, while at the same time having sufficient rigidity for straightening out these passageways and passing through occlusions or other obstacles.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A coupling wire guide for coupling to a previously introduced wire guide during intracorporeal procedures, the coupling wire guide comprising:
a main body having a distal section including an outer wire coiled around a safety wire; and
a loop wire directly connected to the main body at two axially spaced points proximate the distal section to define a loop area extending between the two axially spaced points, the loop area sized to receive the previously introduced wire guide, the loop wire projecting through adjacent winds of the coiled outer wire.

2. The coupling wire guide of claim 1, wherein the length of the loop wire is greater than or equal to a distance between the two axially spaced points as measured along a center line axis of the safety wire.

3. The coupling wire guide of claim 1, wherein the length of the loop wire is greater than or equal to a sum of a distance between the two axially spaced points as measured along a center line axis of the safety wire plus a circumference of the previously introduced wire guide.

4. The coupling wire guide of claim 1, wherein an end portion of the safety wire forms the loop wire.

5. The coupling wire guide of claim 4, wherein the end portion of the safety wire projects away from the outer wire, extends proximally along the outside of the outer wire, and projects back within the outer wire.

6. The coupling wire guide of claim 1, wherein the safety wire is connected to an end cap defining a distal tip of the coupling wire guide.

7. The coupling wire guide of claim 6, wherein the end cap includes a passageway through which the loop wire extends.

8. The coupling wire guide of claim 1, wherein at least a portion of the main body is a mandrel.

9. The coupling wire guide of claim 8, wherein a distal portion of the mandrel narrows to form a safety wire, and wherein the distal section includes an outer wire disposed over the safety wire.

10. The coupling wire guide of claim 1, wherein a portion of the main body comprises the outer wire disposed over the safety wire.

11. The coupling wire guide of claim 1, wherein the loop wire projects through adjacent winds of the coiled outer wire at two locations proximate the two axially spaced points.

12. The coupling wire guide of claim 1 wherein the loop wire is fixedly connected to the main body at two axially spaced points.

13. A coupling wire guide for coupling to a previously introduced wire guide during intracorporeal procedures, the coupling wire guide comprising:
a main body having a distal section; and
the distal section including an outer wire coiled around a safety wire, the safety wire connected to an end cap defining a distal tip of the coupling wire guide, an end portion of the safety wire projecting radially outwardly from the distal tip and then extending proximally along the outside of the outer wire to define a loop area proximal to the distal tip and sized to receive the previously introduced wire guide, an end of the safety wire positioned inside the outer wire and connected to the safety wire wherein the safety wire projects through adjacent winds of the coiled outer wire.

14. The coupling wire guide of claim 13, wherein the end cap includes a passageway through which the loop wire extends.

15. The coupling wire guide of claim 14, wherein the passageway opens onto a radially facing side of the end cap.

16. The coupling wire guide of claim 13, wherein the portion of the safety wire positioned outside of the outer wire is sized to permit the main body and distal section to extend in a straight axial line while maintaining a loop area sized to receive the previously introduced wire guide.

* * * * *